United States Patent
Taubmann et al.

(10) Patent No.: US 12,417,542 B2
(45) Date of Patent: Sep. 16, 2025

(54) METHOD, DEVICE AND COMPUTER-READABLE MEDIUM FOR MAPPING A THREE-DIMENSIONAL BRANCHED TUBULAR STRUCTURE INTO AT LEAST ONE TWO-DIMENSIONAL IMAGE PLANE

(71) Applicant: Siemens Healthcare GmbH, Erlangen (DE)

(72) Inventors: Oliver Taubmann, Weilersbach (DE); Hendrik Ditt, Neustadt an der Aisch (DE); Michael Suehling, Erlangen (DE); Florian Thamm, Fuerth (DE); Leonhard Rist, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 392 days.

(21) Appl. No.: 18/145,106

(22) Filed: Dec. 22, 2022

(65) Prior Publication Data

US 2023/0206453 A1    Jun. 29, 2023

(30) Foreign Application Priority Data

Dec. 28, 2021   (EP) ................................. 21217896

(51) Int. Cl.
     *G06T 7/11*      (2017.01)
(52) U.S. Cl.
     CPC ...... *G06T 7/11* (2017.01); *G06T 2207/10072* (2013.01); *G06T 2210/41* (2013.01)

(58) Field of Classification Search
     CPC ............ G06T 7/11; G06T 2207/10072; G06T 2210/41
See application file for complete search history.

(56) References Cited

U.S. PATENT DOCUMENTS

| | | | |
|---|---|---|---|
| 8,202,213 B2 * | 6/2012 | Ito ......................... | A61B 5/065 600/117 |
| 8,331,637 B2 * | 12/2012 | Bar-Aviv ............... | G16H 50/20 382/128 |
| 8,675,931 B2 * | 3/2014 | Ye ......................... | G06V 10/763 382/128 |
| 9,792,729 B2 | 10/2017 | Kaufman et al. | |
| 10,768,259 B2 * | 9/2020 | Taher ..................... | A61B 5/489 |
| 11,348,250 B2 * | 5/2022 | Koster .................. | A61B 5/004 |
| 11,361,429 B2 * | 6/2022 | Dournes ............... | G06T 7/0012 |
| 11,551,353 B2 * | 1/2023 | Golden .................. | G06V 10/82 |
| 11,847,819 B2 * | 12/2023 | Vilsmeier ............. | G06V 20/698 |
| 2022/0101535 A1 | 3/2022 | Thamm et al. | |

OTHER PUBLICATIONS

Jianu R et al: "Exploring Brain Connectivity with Two-Dimensional Neural Maps", IEEE Transactions on Visualization and Computer Graphics, IEEE, USA, vol. 18, No. 6, Jun. 1, 2012 (Jun. 1, 2012), pp. 978-987; XP011447953; ISSN: 1077-2626, DOI: 10.1109/TVCG.2011.82.

(Continued)

*Primary Examiner* — Gregory M Desire
(74) *Attorney, Agent, or Firm* — Harness, Dickey & Pierce, P.L.C.

(57) ABSTRACT

A computer implemented method maps a three-dimensional branched tubular structure depicted in a three-dimensional image data set into at least one two-dimensional image plane.

20 Claims, 4 Drawing Sheets

(56) References Cited

OTHER PUBLICATIONS

Termeer M. et al.:Comprehensive Visualization of Coronary Artery Disease. IEEE transactions on visualization and computer graphics, 13. 1632-9. IEEE Transactions on Visualization and Computer Graphics ( vol. 13, Issue: 6, Nov.-Dec. 2007).
Kreiser Julian et al; "A Survey of Flattening-Based Medical Visualization Techniques"; Computer Graphics Forum; vol. 37; No. 3; DOI: 10.1111/cgf.13445; pp. 597-624; 2018;.
Gabriel Mistelbauer et al: "Centerline reformations of complex vascular structures", Pacific Visualization Symposium (Pacificvis), 2012 IEEE, IEEE, Feb. 28, 2012 (Feb. 28, 2012), pp. 233-240, XP032166298, DOI: 10.1109/PACIFICVIS.2012.6183596 ISBN: 978-1-4673-0863-2.
Kanitsar, Armin et al. "CPR-Curved Planar Reformation"; Published by IEEE Visualization Oct. 27-Nov. 1, 2002. Boston, MA, USA (pp. 37-44).
Wikipedia, Circle of Willis, https://upload.wikimedia.org/wikipedia/commons/2/2e/Circle_of_Willis_en.svg.

* cited by examiner

METHOD, DEVICE AND COMPUTER-READABLE MEDIUM FOR MAPPING A THREE-DIMENSIONAL BRANCHED TUBULAR STRUCTURE INTO AT LEAST ONE TWO-DIMENSIONAL IMAGE PLANE

CROSS-REFERENCE TO RELATED APPLICATION(S)

The present application claims priority under 35 U.S.C. § 119 to European Patent Application No. 21217896.6, filed Dec. 28, 2021, the entire contents of which are incorporated herein by reference.

FIELD

One or more example embodiments of the present invention concerns a computer implement method for mapping a three-dimensional branched tubular structure depicted in a three-dimensional image data set into at least one-two-dimensional image plane. Additionally, the invention concerns a device, a computer program and a computer-readable storage medium.

RELATED ART

Many imaging processes used in medical imaging, e. g. computed tomography and magnetic resonance imaging, can provide three-dimensional image data sets. While these image data sets can provide a lot of information, extracting the relevant data from a three-dimensional image data set can required quite a bit of manual interaction such as scrolling through slices or rotating the view.

To allow for a comprehensive overview of all relevant parts of an anatomical structure without an elaborate interaction, a so called flattened or unfolded view can be used, in which selected structures, e. g. a vasculature, are mapped to a two-dimensional plane or a given three-dimensional surface.

Multiple methods have been proposed to computer appropriate mappings from a three-dimensional image data set to a two-dimensional image plane for various use cases. For relatively simple structures, e. g. single vessels, a curved planar reformation is commonly used, that is e. g. discussed in Kanitsar, A. et al., CPR—Curved planar reformation, Proceedings of the IEEE Visualization Conference. 37-44. 10.1109/VISUAL.2002.1183754 (2002).

For other tasks, e. g. for imaging the left ventricle of the heart, projections based on spherical, cylindrical or polar coordinates can be used. These are e. g. discussed in Kreiser, J. et al., A Survey of Flattening-Based Medical Visualization Techniques, Computer Graphics Forum, 37:597-624 (2018) and in Termeer, M. et al., CoViCAD: Comprehensive Visualization of Coronary Artery Disease, IEEE transactions on visualization and computer graphics, 13. 1632-9. 10.1109/TVCG.2007.70550, (2007).

SUMMARY

The known processes for flattening three-dimensional image data into a single image can typically not be used successfully for complex branched structures. E. g. none of the discussed approaches can successfully unfold a brain vasculature.

The problem to be solved is therefore to provide an alternate approach for mapping features of a three-dimensional image data set into at least one two-dimensional image plane, that especially allows for a mapping of complex branched structures, e. g. of a brain vasculature.

According to one or more example embodiments, a computer implemented method for mapping a three-dimensional branched tubular structure in a three-dimensional image data set into at least one two-dimensional image plane, includes selecting a first group of voxels in the image data set based on segmentation data, the segmentation data describing a segmentation of the tubular structure in the image data set; determining a respective transformation vector for each voxel of the first group using a given model, the given model specifying a respective position of at least part of the tubular structure in a respective image plane of the at least one two-dimensional image plane, wherein the respective transformation vector maps the respective voxel to the respective image plane; selecting a second group of voxels in the image data set based on at least one of the image data set or the segmentation data, and determining a respective transformation vector for each voxel of the second group that maps the respective voxel to the image plane or a respective image plane, wherein at least one of the selection of the second group of voxels or the determination of the transformation vectors for the second group of voxels is performed by optimizing a cost function based on the transformation vectors for the first group of voxels; and generating at least one output image for the at least one image plane based on the first group of voxels, the second group of voxels, the transformation vectors for the first group of voxels and the transformation vectors for the second group of voxels.

According to one or more example embodiments, the given model describes positions of centerlines of multiple segments of the tubular structure in the at least one image plane, and the selecting the first group of voxels selects voxels corresponding to at least a subgroup of the centerlines the first group of voxels based on the segmentation data.

According to one or more example embodiments, at least one of a sum of a number of voxels for the first group of voxels and the second group of voxels is equal to a number of pixels in the at least one output image, or the voxels the first group of voxels and the second group of voxels are mapped onto a regular, rectangular grid for each image plane.

According to one or more example embodiments, the cost function includes a measure for a smoothness of a transformation from the three-dimensional image data set to the at least one two-dimensional image plane, the transformation being defined by the transformation vectors for the voxels of the first group and the transformation vectors for the voxels of the second group.

According to one or more example embodiments, the method further includes determining a vector field for the transformation from the transformation vectors for the voxels of the first group and the transformation vectors for the voxels of the second group, wherein the measure for the smoothness is based on at least one of a first derivative of the vector field or a second derivative of the vector field.

According to one or more example embodiments, for at least a subgroup of the second group of voxels the cost function is based on a distance of a respective voxel of the subgroup in the respective image plane of the at least one two-dimensional image plane from a position of at least voxel of the first group in the respective image plane or from at least one respective centerline described by the given model.

According to one or more example embodiments, the cost function is based on a measure for a symmetry of the at least one output image.

According to one or more example embodiments, the cost function is based on a brightness of the at least one output image.

According to one or more example embodiments, the selecting the second group of voxels selects the second group of voxels based on at least one of a brightness of the respective voxel, a proximity of the respective voxel to a voxel of the first group, a previously selected voxel of the second group, a segment of the image data set that is identified as part of the tubular structure, or a centerline of a segment of the tubular structure.

According to one or more example embodiments, the method further includes selecting one of a number of provided models based on at least one of the image data set or the segmentation data, the selected model at least one of (i) is used to determine the respective transformation vector for each voxel of the first group, or (ii) is parametrized based on at least one of the image dataset or the segmentation data.

According to one or more example embodiments, the image dataset is a computed tomography dataset.

According to one or more example embodiments, the at least one output image is used as at least one of desired output data to train an algorithm by machine learning or input data of an algorithm trained by machine learning to determine at least one parameter of the three-dimensional branched tubular structure.

According to one or more example embodiments, a device for mapping a three-dimensional branched tubular structure depicted in a three-dimensional image data set into at least one two-dimensional image plane, is configured to perform a computer implemented method according to one or more example embodiments.

According to one or more example embodiments, a non-transitory computer-readable storage medium comprises instructions which, when executed by a data processing unit, cause the data processing unit to perform a computer implemented method according to one or more example embodiments.

BRIEF DESCRIPTION OF THE DRAWINGS

Features of one or more example embodiments of the present invention will become apparent from the following detailed description considered in conjunction with the accompanying drawings. The drawings, however, are only principle sketches designed solely for the purpose of illustration and do not limit the invention. The drawings show.

DETAILED DESCRIPTION

A problem is solved by the initially discussed computer implemented method, comprises the steps:

Selecting a first group of voxels in the image data set based on segmentation data that describes a segmentation of the tubular structure in the image dataset, Determining a respective transformation vector for each voxel of the first group using a given model that specifies the respective position of at least part of the tubular structure in the or a respective image plane, wherein the respective transformation vector maps the respective voxel to the image plane or the respective image plane, Selecting a second group of voxels in the image data set, especially based on the image data set and/or the segmentation data, and determining a respective transformation vector for each voxel of the second group that maps the respective voxel to the image plane or a respective image plane, wherein the selection of the second group of voxels and/or the determination of the transformation vectors for the second group of voxels is performed by optimizing a cost function that depends on the transformation vectors for the first group of voxels, and Generating an output image for the at least one image plane based on the first and second group of voxels and the transformation vectors for the first and second group of voxels.

The inventive method according to one or more example embodiments uses a hybrid approach, in which segmentation data, especially provided labels for certain segments, is used to select a first group of voxels, that are then transformed using a given model. The mapping and/or selection of a second group of voxels is based on solving an optimization problem.

Since the voxels of the first group are mapped using a given model, this mapping can essentially be of arbitrary complexity. It is e. g. possible to define a certain area of the two-dimensional image plane, into which voxels of a segment with a certain label, that are e. g. associated with a certain vessel or its centerline, are mapped. Since further voxels, especially voxels for which a clear segmentation might not be possible, are mapped by solving an optimization problem, the resulting transformation can conform quite well to desired properties, e. g. by providing a smooth transformation, the inclusion of voxels with certain properties, a conservation of relative distances to a certain degree, etc.

The use of the given model as part of the transformation also typically allows for the resulting output image to closely resemble depictions of the relevant structure, that are well-known to the skilled person, e. g. to depictions used in common textbooks. It is e. g. possible, to map the vasculature of the brain approximately to the Circle of Willis and therefore to a well-known textbook representation of this vasculature.

The additional mapping of the second group of voxels can then be used to include structures into the output image that cannot be mapped directly to the model, e g. smaller branches of the tubular structure, surrounding tissue, etc.

The input data of the method, namely the image data set and/or the segmentation data can be received by an interface, e. g. of a computer program or part of a computer program or by a hardware interface. The measurement of the image data set can be performed prior to the beginning of the claimed method or as part of the claimed method. The segmentation data can also be provided prior to the claimed method or as part of the method.

Segmentation data can e. g. be provided by manual or automatic segmentation of the image data set. Preferably the segmentation data also comprises labels for at least some of the segments, e. g. for at least some segments of the branched tubular structure or its centerlines. The segmentation data can therefore preferably describe the centerlines of at least part of the branched tubular structure and especially its topology, e. g. which segments and therefore centerlines are connected to each other.

The selection and mapping of the second group of voxels can be optimized in such a way, that each voxel transformed into the image plane corresponds to a single pixel of the output image. It is however also possible, that the number of voxels mapped to the image plane is different than the number of pixels in the output image. In this case, it is e. g. possible that the output image is generated by resampling the voxels in the image plane, e. g. by interpolating between voxels within a certain area around the pixel. It is also possible, that certain areas in the output image do not have any voxels mapped thereto and therefore e. g. have a fixed background color.

The output image can e. g. be directly output to a monitor, written to a data base, transmitted via a network, etc. The output image can allow a user to instantly recognize relevant structures, e. g. occlusions in vessels, without the necessity to look through a multitude of protections and/or sectional planes. Even when multiple output images are generated, it is typically faster and easier to switch through a relatively low number of output images than to analyze a complex three-dimensional image data set.

The branched tubular structure can e. g. be a brain vasculature, a liver vasculature or a none-vascular branched tubular structure, e. g. bronchial tubes or a section of the nerve tract.

As previously discussed, the segmentation data can be based on a manual segmentation and especially labeling by a user. For many branched tubular structures, e. g. those structures discussed above, approaches for automatic or at least semi-automatic segmentation and labeling are also known and therefore there is potentially no or only limited user action necessary for the segmentation and/or labeling. The segmentation data preferably provides a graph representing the centerlines of the tubular sections and their connections. This graph can e. g. be generated from a segmentation that is provided as a bit mask of the image data set or by a similar means by the use of approaches like vessel tracing or more generally tubular section tracing and atlas based methods that are in principal known in the art and already used for segmentation and labeling of such structures.

The model can describe the positions of centerlines of multiple segments of the tubular structure in the at least one image plane, wherein voxels corresponding to at least a subgroup of the centerlines can be selected as the first group of voxels based on the segmentation data and mapped to the respective centerline in the or the respective image plane. As previously discussed, the segmentation data can directly describe the centerlines and therefore immediately allow for a selection of the corresponding voxels. Preferably the segmentation data can comprise a label for voxels or groups of voxels or such a label can be generated on the fly based on the segmentation data and/or the three-dimensional image data and used to identify voxels that are part of the centerline. Once the voxels that are part of a respective centerline are identified, the model therefore describes a mapping from a liner structure in the three-dimensional image data set to a liner structure in the image plane and the transformation vector for the respective voxel can therefore be determined from the position of the voxel along the identified centerline in the image data set.

The number of voxels for the second group can be chosen such, that the sum of the number of voxels for the first and second group is equal to the number of pixels in the output image. Preferably for each pixel in the output image a single voxel from the image data set is selected and transformed to the pixel position. With this approach the use of resampling and interpolation can be avoided and therefore the output image can be a high quality image without any blurring or similar artefacts.

Alternatively, or additionally the transformation vectors can be chosen in such a way, that the voxels of the first and second group are mapped onto a regular, rectangular grit for the or each image plane. This can be achieved by the previously discussed mapping of each voxel to a corresponding pixel position. It is however also possible, that the grid of voxels mapped to the image plane does have a higher or lower resolution then the output image. In this case a resampling, e. g. based on interpolation, can be used.

It is e. g. possible to continue selecting voxels for the second group, until a desired number is reached. The selection of a respective voxel or a group of voxels can be optimized individually. It is e. g. possible to optimize the selection in such a way, that the respective voxel can be smoothly mapped to a free pixel and is preferably close to the original position of an already mapped voxel and/or has a high brightness. It is also possible to select the voxels of the second group by using a global optimization approach, e. g. by optimizing the brightness of the output image as discussed below.

The cost function can be or comprise a measure for the smoothness of the transformation from the three-dimensional image data set to the at least one two-dimensional plane defined by the transformation vectors for the voxels of the first and second group. An optimization for smoothness is a global optimization that also ensures desirable local properties e. g. that voxels that are in close proximity to each other in the image data set will also be mapped to close points in the image plane if possible.

Additionally, or alternatively the optimization can be performed using a boundary condition that ensures that the transformation is differentiable. A differentiable transformation typically allows for an inversion of the transformation, which can e. g. be used to locate the position of a certain feature in the three-dimensional image space once it is located in the output image. Using a differentiable transformation can also be advantages, when the output image is further processed by an algorithm that is to be trained by machine learning. In this case optimization approaches that require a differentiable algorithm can also be extended to also optimize the transformation.

The cost function can also incorporate costs for mapping voxels to positions that deviate from a regular grid and/or that penalize the mapping of multiple voxels to the same pixel. Alternatively or additionally, the optimization can include the selection of exactly one respective voxel that is mapped to each pixel or similar approaches that ensures that selected voxels do not overlap after being mapped to the image plane. When selecting a respective voxel for each pixel, the selection of the voxel automatically determines the transformation vector.

A vector field for the transformation can be determined from the transformation vectors for the first and second group of voxels, wherein the measure for the smoothness depends on the first and/or second derivative of the vector field. The vector field can be a two-dimensional vector field, e. g. when a respective voxel is selected for each pixel of the output image or by interpolating between the transformation vector of the different voxels mapped to the image plane. If multiple image planes are used, a stack of these image planes, essentially defining a three-dimensional space, or an arrangement of the image planes at an angle to each other around a common axis that is included in each image plane can be considered, providing a three-dimensional vector field.

Alternatively, the vector field can be determined in the three-dimensional space of the image data set, e. g. by interpolating the transformation vectors between the voxels for which a respective transformation vector is determined.

The magnitudes of the first and/or the second derivatives can e. g. be summed, especially as a weighted sum, over the image plane or the three-dimensional space discussed above and then used as a cost function or as part of the cost function.

For at least a subgroup of the second group of voxels the cost function can depend on the distance of the respective voxel of this sub group in there or the respective image plane from the position of at least one respective voxel of the first group in the or the respective image plane or from at least one respective centerline described by the model. The voxels of the second group can e. g. be selected to be close to voxels of the first group, e. g. to voxels of a centerline. In this case the previously discussed condition ensures that this closeness is conserved after the mapping to the image plane. The cost function can especially be chosen in such a way, that the relative distances in the image data set between voxels are at least approximately conserved after the voxels are mapped to the image plane. Especially relative distances of different voxels to a given centerline can be conserved as far as possible.

The cost function can depend on a measure for the symmetry of the at least one output image. The measure for the symmetry can especially be a measure for a mirror symmetry with respect to a given symmetry axis. The symmetry axis can e. g. be defined by the model. Relevant tubular structures and especially their representation in the literature are often symmetric. Therefore, this additional condition can help to replicate the real structure in the output image and can also provide an output image that is closer to an expected result.

The cost function can additionally or alternatively depend on the brightness of the at least one output image. When imaging a branched tubular structure in medical imaging, the structure will typically be either notably brighter or notably less bright than the surrounding tissue. To achieve this effect e. g. in computed tomography angiography, it is known to use a contrast agent that is previously injected into the vasculature. By optimizing the brightness of the output image, the optimization algorithm and favors the selection of e. g. brighter voxels that e. g. in a computed tomography angiography typically corresponds to parts of the vasculature. This approach therefore in ensures that, as much of the branched tubular structure as possible is depicted in the at least one output image, even for sections of the branch tubular structure that are not correctly identified by the segmentation data, e. g. for small vessels.

The second group of voxels can be selected depending on at least one property of the respective voxel, namely the brightness of the respective voxel and/or the proximity of the respective voxel to a voxel of the first group and/or to a previously selected voxel of the second group and/or to a segment of the image data set that is identified as part of the tubular structure and/or as a centerline of a segment of the tubular structure. It is especially possible to iteratively select additional voxels of the second group, favoring bright voxels starting from voxels that are close to the first group of voxels or the centerline and extending outward, to include such voxels, that might be part of the tubular structure but that are potentially not identified as part of the tubular structure during the segmentation of the image data set. In general, voxels close to the tubular structure can also be included independent of their brightness, e. g. to use areas of the output image that are not required to depict the tubular structure itself to depict the surrounding tissue.

It is possible to provide several models, wherein one of the provided models is selected based on the image data set and/or the segmentation data and used to determine the respective transformation vector for each voxel of the first group. Different models can e. g. cover different normal anatomical variants. The relevant model or variant can then e. g. be selected based on the presence or absence of certain sub structures of the tubular structure, e. g. a certain vessel. The presence of sub structures of the tubular structure can easily be detected when the segmentation data comprises a label for at least some of the segments. It can e. g. simply be checked if a certain label is present or not. Alternatively, such a label can be generated on the fly, e. g. using an anatomical atlas and/or vessel tracing.

Additionally or alternatively, the model used to determine the respective transformation vector for each voxel of the first group can be parametrized based on the image data set and/or the segmentation data. Such a parametrization can e. g. be used to take variations of the diameter and/or length of certain sub structures, e. g. certain vessels, into account.

The image data set can be a computed tomography data set, especially a computed tomography angiography data set or a computed tomography perfusion data set, or a magnetic resonance data set, especially a magnetic resonance angiography data set. It was found, that the described mapping is especially relevant and robust for the mentioned data sets.

The at least one output image can be used as desired output data to train an algorithm by machine learning. In this case the method can also be considered a method for training an algorithm using machine learning. In this context one or more example embodiments of the present invention is also directed toward a trained algorithm provided by this method, a parameter set determined during the training of the algorithm to parametrize a given algorithm and/or a computer-readable storage medium storing the trained algorithm or the parameter set.

The machine learning can e. g. be a supervised learning that uses training data sets that comprise a respective three-dimensional image data set and segmentation data as input data and the respective output image as desired output data. In this case the algorithm can be trained to perform a mapping that is similar to the mapping performed by the described method, wherein and algorithm trained by machine learning can potentially be more CPU efficient than an optimization algorithm. In an advantageous variant the input data in the training data set can already describe the selected first group of voxels and their transformation, especially the transformation vectors. In this case the algorithm can be trained to perform the selection and transformation of the second group of voxels and therefore the part of the method that is otherwise performed by a typically CPU intensive, optimization algorithm.

Additionally or alternatively, it is possible to use the at least one output image as input data of an algorithm trained by a machine learning to determine at least one parameter of the three-dimensional branched tubular structure. In this case the algorithm can e. g. be trained to detect an occlusion in a vascular structure or other types of potentially medical relevant irregularities in the tubular structure. The algorithm can therefore e. g. be used to supporter a user in forming a diagnosis.

A major advantage of using the at least one output image as input data for such an algorithm instead of the full three-dimensional data set is the ability to notably reduced the amount of input data processed by the algorithm. This also reduces the complexity of the trained algorithm, e. g. the number of input nodes in a neuronal network, and therefore the number of free parameters that need to be trained during the machine learning. This can lower the number of training data sets required for a robust training of the algorithm.

As previously discussed, the mapping of the voxels of the first and second group to the output image is preferably differentiable. This especially allows for using the transformation as a starting point and then perform a common training of the transformation and the algorithm. It is e. g. possible to vary the voxel selection and/or the used transformation vectors of voxels to minimize a cost function for the output of the algorithm trained by machine learning, e.g. during a backpropagation of error.

In general, an algorithm trained by machine learning can mimic cognitive functions that humans associate with other human minds. In particular, by training based on training data the trained algorithm is able to adopt to new circumstances and detect and extrapolate patterns.

In general, parameters of the algorithm can be adapted via training. In particular, supervised training, semi-supervised training, unsupervised training, reinforcement learning and/ or active learning can be used. Furthermore, representation learning, also called feature learning, can be used. In particular, the parameters of the algorithm can be adapted iteratively by several steps of training.

In particular, a trained algorithm can comprise a neuronal network, a support vector machine, a decision tree and/or a Bayesian network. Additionally or a alternatively, the trained algorithm can be based on k-means clustering, Q-learning, genetic algorithms and/or association rules. In particular, a neuronal network can be a deep neuronal network, a convolutional neuronal network or a convolutional deep neuronal network. Furthermore, a neuronal network can be an adversarial network, a deep adversarial network and/or a generative adversarial network.

Besides the inventive computer implemented method, one or more example embodiments of the present invention concerns a device for mapping a three-dimensional branched tubular structure depicted in a three-dimensional image data set into at least one two-dimensional image plane, wherein the device comprises means for carrying out the inventive computer implemented method according to one or more example embodiments. The device can comprise an interface for receiving input data, especially the image data set and/or the segmentation data, and/or an interface for providing output data, especially the at least one output image. The interface for receiving the input data and for providing the output data can be the same interface. The interface can be a software interface, e. g. an interface between a program or a part of a program that implements the method and a further program or program part implemented on the same device. It is also possible to that the respective interface is a hardware interface, e. g. a network connection.

The device can be implemented by using a data processing unit to execute a computer program implementing the method. The data processing unit can e. g. be a work station, a server, a cloud-based solution or an embedded device that can e. g. be integrated into a medical imaging device.

Additionally, one or more example embodiments of the present invention concerns a computer program comprising instructions which, when the program is executed by a data processing unit, cause the data processing unit to carry out an inventive method according to one or more example embodiments.

Additionally, one or more example embodiments of the present invention concerns a computer-readable storage medium having stored thereon on a computer program according to one or more example embodiments of the present invention.

The device, computer program and/or computer-readable storage medium can especially implement the previously discussed embodiment of the method, that is used to train an algorithm by machine learning.

In particular, the features and advantages described in connection with the computer implemented method according to one or more example embodiments of the present invention can also be designed as corresponding subunits of the device according to one or more example embodiments of the present invention or of the computer program according to one or more example embodiments of the present invention. Conversely, the features and advantages described in connection with the device according to one or more example embodiments of the present invention or the computer program according to one or more example embodiments of the present invention can also be designed as corresponding process steps of the process according to one or more example embodiments of the present invention.

Figure 1:
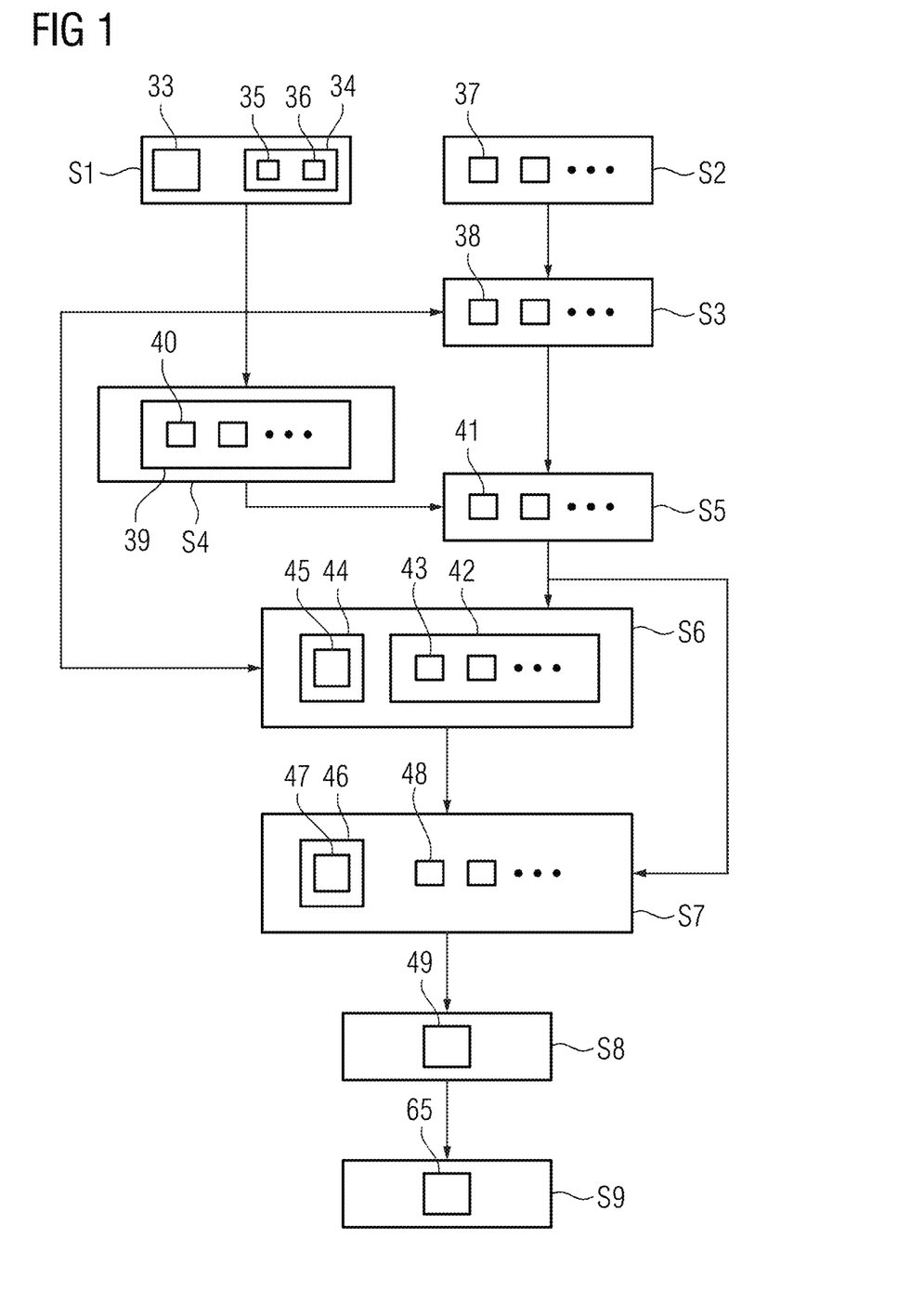
FIG. 1 a flow chart of an exemplary embodiment of a computer implemented method for mapping a three-dimensional branched tubular structure depicted in a three-dimensional image data set into a two-dimensional image plane to generate an output image, additionally showing relevant algorithms and data structures, FIG. 2 an example of using a model for mapping voxels into the image plane, FIG. 3 an exemplary embodiment of a device for mapping a three-dimensional branched tubular structure into a two-dimensional image plane, and FIGS. 4 and 5 examples of algorithms that can be trained using the output image as desired output data and/or that can use the output image as input data.

FIG. 1 shows the flow chart of a method for mapping a three-dimensional branched tubular structure 73 depicted in a three-dimensional image data set 33 into a two-dimensional image plane 50 to generate an output image 49. As will be discussing in more detail below, respective transformation vectors 41, 48 are determined for transforming a first group 39 of voxels 40 and a second group 42 of voxels 43 of the image data 33 into a two-dimensional image plane 50.

Figure 2:
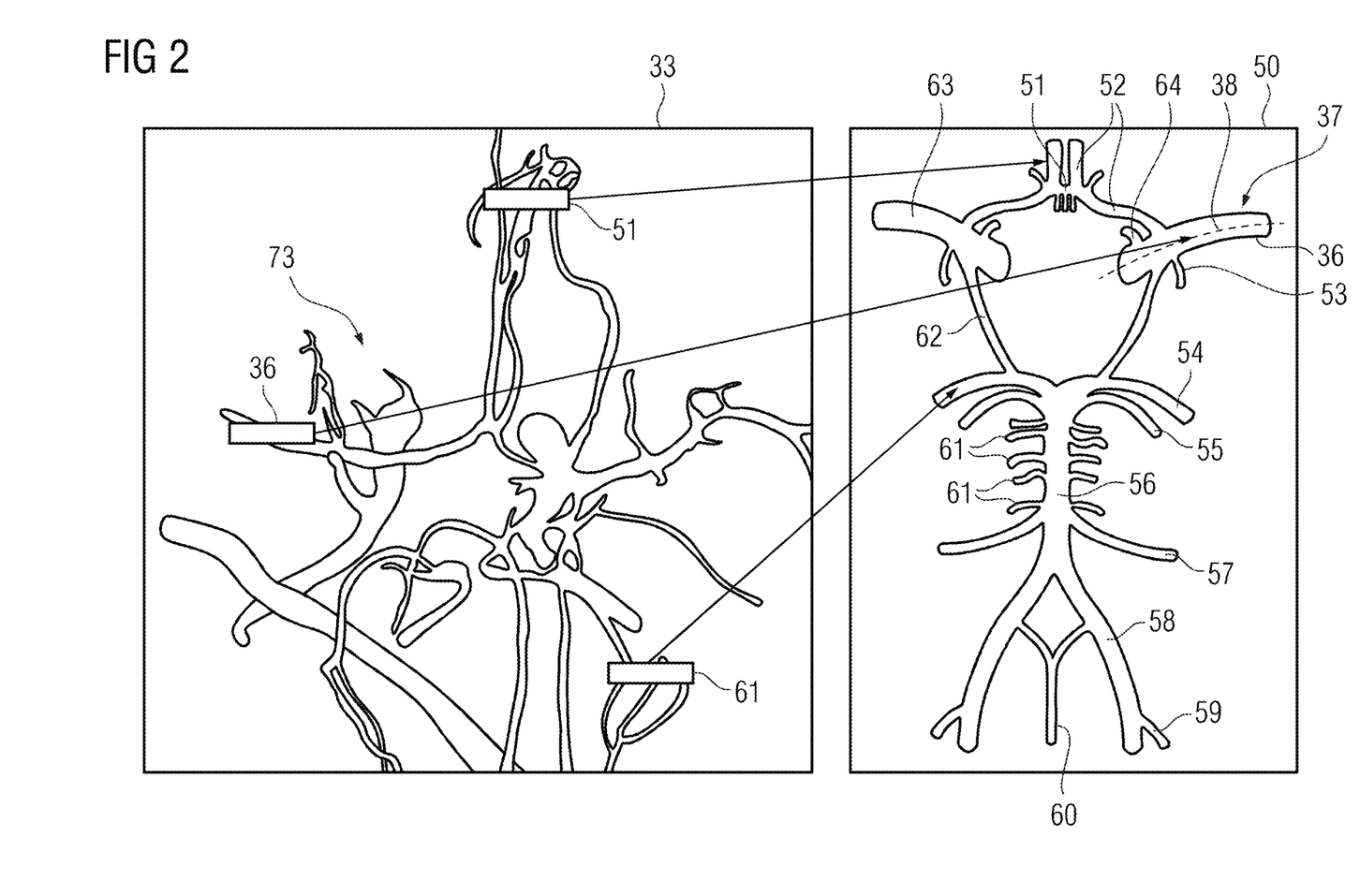

As schematically shown in FIG. 2, a model 37 is used to map the voxel 40 of the first group 39 to the image plane 50. The model 37 describes the areas in the image plane 50 that correspondent to certain segments 35 of the structure 73. In the example, it is assumed, that the segmentation data 34 provides a respective label 36, 51-64, for at least some of the segments 35 of the structure 73, especially for the centerlines 38 of the major vessels or other major segments of the structure 73.

Since the same labels 36, 51-64 are also used in the model 37, voxels in labelled segments 34, e. g. voxels along the centerlines of major vessels or other segments of the structure 73, can be directly mapped to the image plane 50 using the model 37.

Additional voxels 43 of a second group 42 are then selected and mapped using an optimization algorithm. An exemplary embodiment of such a method will now be discussed with reference to the individual steps in FIG. 1.

In step S1 the image data set 33 and segmentation data 34 describing several segments 35 and corresponding labels 36, 51-63 in the three-dimensional image data set 33 are determined or received. It is e. g. possible to record the image data set 33 prior to applying the method, e. g. using computed tomography angiography or magnetic resonance angiography.

The segmentation and labelling to provide the segmentation data 34 can also be performed prior to the beginning of the method, e. g. by manually segmenting and labelling the data set 33 or by other well-known approaches for an automatic or semi-automatic segmentation and labelling.

Alternatively, it would be possible, to generate the segmentation data 34 on the fly in step S1, e. g. by determining a preliminary segmentation and labelling using a brain atlas containing a probabilistic map of these vessels that is registered to the scan and then further refine the segmentation and labelling, such as to resolve protentional ambiguities in the assignment, by tracing the vessel tree graph from confidentially identified bifurcations and performing rule-based attribution of vessel labels based on anatomical prior knowledge of potential variations.

In step S2 multiple models 37 are provided in the example. It is e. g. possible to provide a respective model 37 for each of several known normal anatomical variations.

In step S3 one of the models 37 is selected and later used to describe positions of the centerlines 38 of multiple segments 34 of the tubular structure 33 in the image plane 50. The selection of the model 37 to be used can e. g. be based on the segmentation data 34. It is especially possible, that at least some of the variants described by the models 37 differ in the presence or absence of certain segments with certain labels. Therefore, it can e. g. simply be checked, if certain labels are present in the segmentation data 34 and dependent on the presence of these labels 36, one of the models 37 can be selected.

Alternatively or additionally, the selection of the models 37 could e. g. be based on the image data set 33 itself and/or on additional information, e. g. the age and/or weight of the patient.

In step S4 a first group 39 of voxels 40 is selected based on the segmentation data 34. It is e. g. possible to select all voxels in segments 35 that have a label 36 for which the position of the centerline 38 is known from the model. Since the position of the respective voxel 40 along the respective centerline can be easily determined from the segmentation data 34 and the position of the respective centerline 38 in the image plane 50 is known from the used model 37, a transformation vector for each of the voxels 40 can be directly calculate in step S5. This approach is schematically illustrated in FIG. 2 for the sections with the labels 36, 51 and 61.

After step S5 the image plane 50 is very sparsely populated, since only voxels 40 that are part of a centerline 38 are mapped to the image plane 50 by the model 37. To provide a user with as much information as possible when only looking at the output image 49 generated based on voxels 40, 43 transformed to the image plane 50, a second group 42 of voxels 43 is selected in step S6 and a respective transformation vector 48 determined for each of these voxels 43 in step S7.

In the example shown in FIG. 1 each of these steps comprises an optimization, especially the maximization or minimization, of a respective cost function 45, 47 by an optimization algorithm 44, 46. Therefore, in the example the selection of the voxels 43 of the second group 42 is completed first and afterwards the transformation vectors 48 for these voxels are determined by a separate optimization.

In alternative implementations these steps can be combined and the selection of the voxels 43 of the second group 42 and the determination of the transformation vectors 48 can be performed in a single step. This can e. g. be the case when a single voxel 40, 43 should be chosen for each pixel of the output image 49 or when some other kind of regular grid of voxels should result in the image plane 50. In these cases, the ideal voxel for each pixel or grid position is selected and therefore the selection of the voxel automatically provides a transformation vector.

In a third alternative, it would e. g. be possible to perform the steps S6 and S7 iteratively. It would e. g. be possible to first select a certain number of voxels 43 of the second group 42, determine transformation vectors 48 for these voxels 43 and then repeat the selection process to select additional voxels 43 of the second group 42 and so on. This can e. g. be useful when some kind of region growing or a similar algorithm is used to select the voxels 43 of the second group 42.

An iterative mapping of individually selected voxels or smaller sub groups of voxels 43 can also be considered to be an ad-hoc approach.

The cost functions 45, 47 can comprise terms that concern the individual voxels or local properties and/or terms that concern global properties.

Concerning the local properties, the selection of a respective voxel 43 in step S6 can e. g. be based on the brightness of the respective voxel 43, the distance of the respective voxel 43 to a voxel 40 of the first group 39 and/or to a previously selected voxel 43 of the second group 42 and/or to a segment of the image data set 33 that is identified as part of the tubular structure 73 and/or as the centerline 38 a segment 35. Concerning these terms of the cost function, it is often desirable to maximize the brightness of the selected voxels 43 of the second group 42 and/or to minimize at least one of the distances discussed above. This can e. g. be archived by choosing different signs for these terms in the cost function.

In principle, also the determination the transformation vectors 48 in step S7 can be based on a purely local optimization. It is e. g. possible, that the cost function 47 depends on the distance of the respective voxel 43 in the image plane 50, and therefore after applying the transformation vector 48, from the position of at least one respective voxel 40 of the first group 39 in the image plane and/or from a centerline 38 descripted by the model 37. It is therefore possible to e. g. select bright voxels and locally optimize the positions of the individual transformed voxels using the cost function 47. This approach allows for a mapping of the local surroundings of the respective centerline and conserves local distances reasonably well.

Preferably, at least one of the cost functions 45, 47 or a common cost function used to optimize the selection and mapping of the voxels 43 of the second group 42 can comprise at least one term concerning a global optimization criterium. Concerning the selection of the voxels 43, it is especially possible that the brightness of the output image is maximized in during the optimization. This can e. g. be useful, since branched tubular structures, e. g. a vessel tree imaged using a contrast agent, can be notably brighter than the surrounding tissue. The optimization of the brightness of the output image therefore leads to a preferred selection of voxels of the image data set 33 that depict parts of the branched tubular structure 73, even when these parts of the structure 73 where not correctly detected during segmentation.

The cost function 47 for determining the transformation vectors 48 or a common cost function that is additionally used to select the voxels 43 of the second group 42 can also comprise at least one global optimization criterium. Preferably, it comprises a measure for the smoothness of the transformation from the three-dimensional image data set 33 to the two-dimensional image plane 50 defined by the transformation vectors 48 for the voxels 40, 43 of the first and second group 39, 42. The use of a smooth transform improves the readability of the resulting output image 49, since the output image is at least locally approximately consistent with the image data set 33 when a smooth transformation is used.

As already described in detail in the general part of the description, the measure for the smoothness can especially depend on the first and/or second durative of a vector field that is determined from the transformation vectors of the first and second group of voxels 40, 43. Such an optimization is even possible, when an iterative approach is used. In this case the position of a newly selected 43 voxel can e. g. be based on interpolating between sparsely defined displacements of surrounding voxels.

As already discussed in the general section of the description, it can also be advantageous to optimize for a symmetric output image. Therefore, the cost functions 45, 47 or a common cost function used for the selection of the voxels 43 and the determination of the transformation vectors 48 can depend on a measure for the symmetry of the output image 49. In this case the calculation of the cost function can involve the generation of an output image or at least an approximate output image. It is e. g. possible to generate a synthetic output image by mirroring one half the output image and then integrate the difference between the synthetic output image and the output image to calculate a term of the cost function 45, 47.

After the selection of all voxels 43 of the second group 42 and the determination of the transformation vectors 48 in the steps S6 and S7 an output image 49 can be generated in step S8. The generation of the output image 49 is trivial, when exactly one of the voxels 40, 43 corresponds to each pixel of the output image 49 after the transformation to the image plane 50. In this case the resulting intensities for the respective pixel can be directly taken from the intensity for the respective voxel. If the resulting grid of voxels in the image plane does not exactly correspond to the pixel grid, it is e. g. possible to resample the image data in the image plane by interpolation between the voxels. It is also possible to assign a fixed background intensity or color to sections of the output image 49 that do not comprise a sufficient density of voxels.

With the generation of the output image 49 in step S8 the descripted method for mapping the branched tubular structure to a two-dimensional image plane is finished. The image 49 could then e. g. be displayed to a user or stored in a data base.

It is however possible, to further use the output image 49 in the optional step S9 in the context of machine learning. A first way to use the output image 49 is to use it as input data for an algorithm 65 that is trained by machine learning to determine at least one parameter of the three-dimensional branched tubular structure 73.

As already discussed in detail in the general part of the description, the use of the output image 49 as input data instead of the use of the full three-dimensional image data set 33 can be advantageous, since the reduction in the amount of input data can reduce the complexity of the algorithm 65 and therefore the amount of required training data. Except for the replacement of the used input data, the training can be performed as usual, e. g. but providing training data sets including the input data of the algorithm 65 as well as a desired result, namely the at least one parameter, that can e. g. be previously determined by an expert in the field or some other algorithm. If the transformation defined by the transformation vectors 41, 48 is differentiable, the training might also include an optimization of the transform.

An alternate approach of using the output image 49 in the context of machine learning is to train the algorithm 65 to perform the transformation or at least part of the transformation discussed above to generate the output image 49 based on the three-dimensional image data set 33 and especially the segmentation data 34. The replacement of the optimization algorithms 44, 46 by a trained algorithm can notably speed up the transformation. As already discussed in the general part of the description, the voxels 40 of the first group 39 and the transformation vectors 41 can be provided as additional input data and therefore the trained algorithm 65 can e. g. only replace the steps S6 and S7.

The discussed approach for generating the output image 49 can be modified to generate multiple output images 49 by mapping the voxels 40, 43 of the first and the second group 39, 42 to multiple image planes 50 and generating an output image 49 for each image plane 50. This can especially be achieved by using a model 37, that maps the voxels 40 of the first group 39 to multiple image planes 50. The optimization based a selection and transformation of the voxels 43 of the second group 42 can then be performed as discussed above. It is however advantageous, when a smoothness of the transformation is to be optimized, to also include derivatives of the vector field orthogonal to the respective image plane, e. g. by stacking the different image planes or by arranging the multiple planes at a given angle to each other. In this case the image planes approximately span a three-dimensional space. Such an arrangement of the image planes also allows to define distances between voxels mapped to different image planes using a measure for three-dimensional distances.

Figure 3:
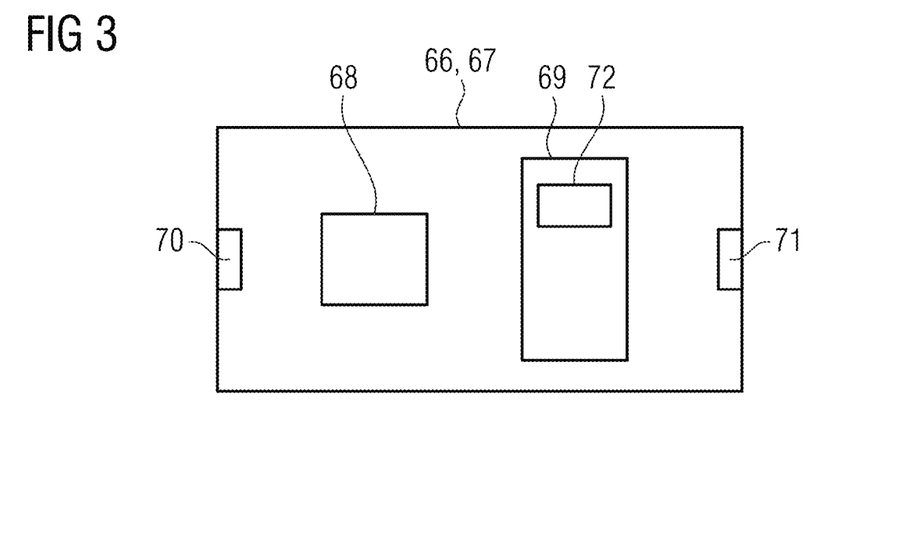

A possible implementation for a device for mapping a three-dimensional branched tubular structure 73 to at least one two-dimensional image plane 50 is shown in FIG. 3. The device 66 is shown as a general-purpose data processing unit 67, that is programed to carry out the previously discussed method. It comprises means 68, 69 for performing the method, namely a processor, e.g. a CPU, as means 68 and a memory as means 69, wherein the memory stores a computer program 72 comprising a instructions that, when the program is executed by the data processing unit 67, causes the data processing unit 67 to carry out the discussed method.

The device can comprise an input interface 70 for providing the input data, especially the three-dimensional image data set 33 and optionally the segmentation data 34. Alternatively, the segmentation data 34 can be generated by the device 66 itself. The output image 49 or data based on the output image 49 can be provided via an output interface 71. It would also be possible, to use the same interface for data input and output or to use software interfaces for at least part of the data exchange.

As previously discussed, the output image 49 can be used as input data or as desired output data for an algorithm 65 trained by machine learning. A common approach to implementing such an algorithm is the use of a neuronal network. Two examples of neural networks that could be used in this step are now discussed with reference to FIGS. 4 and 5, wherein a rather low number of input nodes is shown for the sake of simplicity and clarity. Real implementations will typically comprise a larger number of nodes.

Figure 4:
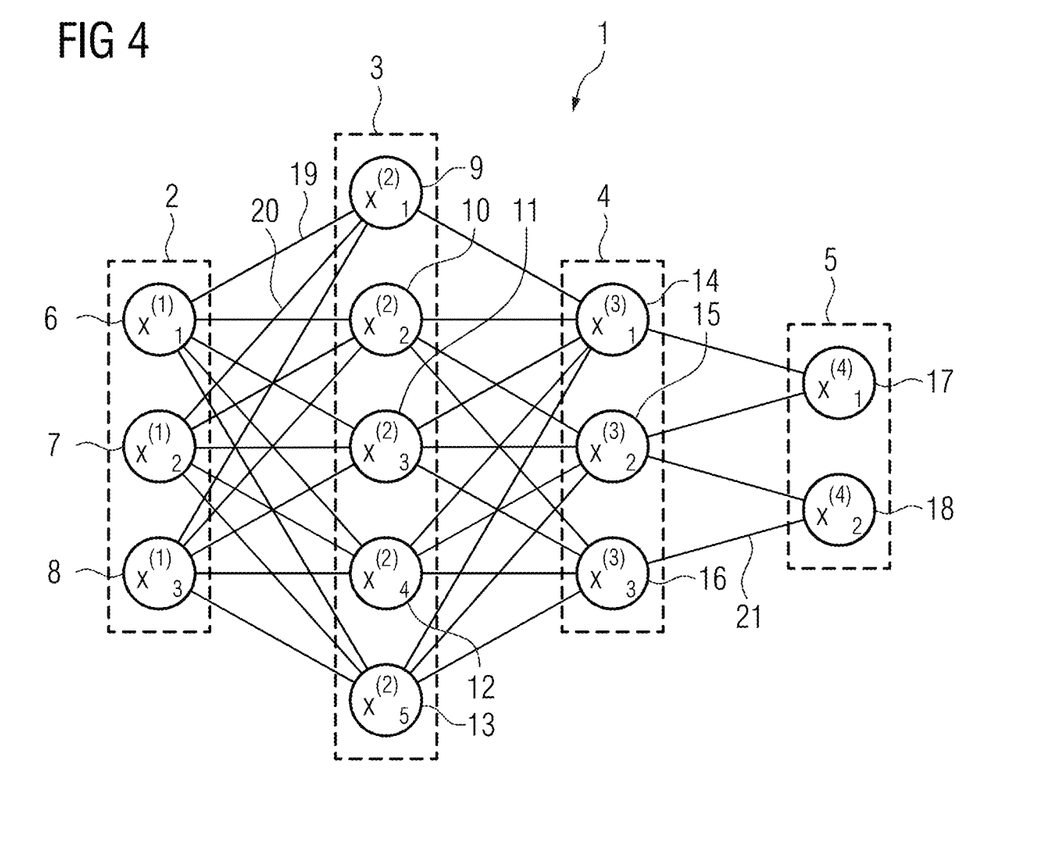

FIG. 4 displays an embodiment of an artificial neural network 1. Alternative terms for "artificial neural network" are "neural network", "artificial neural net" or "neural net".

The artificial neural network 1 comprises nodes 6-18 and edges 19-21, wherein each edge 19-21 is a directed connection from a first node 6-18 to a second node 6-18. In general, the first node 6-18 and the second node 6-18 are different nodes 6-18. It is also possible that the first node 6-18 and the second node 6-18 are identical. For example, in FIG. 4 the edge 19 is a directed connection from the node 6 to the node 9, and the edge 20 is a directed connection from the node 7 to the node 9. An edge 19-21 from a first node 6-18 to a second node 6-18 is also denoted as "ingoing edge" for the second node 6-18 and as "outgoing edge" for the first node 6-18.

In this embodiment, the nodes 6-18 of the artificial neural network 1 can be arranged in layers 2-5, wherein the layers 2-5 can comprise an intrinsic order introduced by the edges 19-21 between the nodes 6-18. In particular, edges 19-21 can exist only between neighboring layers of nodes 6-18. In the displayed embodiment, there is an input layer 2 comprising only nodes 6-8 without an incoming edge, an output layer 5 comprising only nodes 17, 18 without outgoing edges, and hidden layers 3, 4 in-between the input layer 2 and the output layer 5. In general, the number of hidden layers 3, 4 can be chosen arbitrarily. The number of nodes 6-8 within the input layer 2 usually relates to the number of input values of the neural network, and the number of nodes 17, 18 within the output layer 5 usually relates to the number of output values of the neural network.

In particular, a (real) number can be assigned as a value to every node 6-18 of the neural network 1. Here, $x(n)_i$ denotes the value of the i-th node 6-18 of the n-th layer 2-5. The values of the nodes 6-8 of the input layer 2 are equivalent to the input values of the neural network 1, the values of the nodes 17, 18 of the output layer 5 are equivalent to the output values of the neural network 1. Furthermore, each edge 19-21 can comprise a weight being a real number, in particular, the weight is a real number within the interval $[-1, 1]$ or within the interval $[0, 1]$. Here, $w(m,n)_{i,j}$ denotes the weight of the edge between the i-th node 6-18 of the m-th layer 2-5 and the j-th node 6-18 of the n-th layer 2-5. Furthermore, the abbreviation $w(n)_{i,j}$ is defined for the weight $w(n,n+1)_{i,j}$.

In particular, to calculate the output values of the neural network 1, the input values are propagated through the neural network 1. In particular, the values of the nodes 6-18 of the (n+1)-th layer 2-5 can be calculated based on the values of the nodes 6-18 of the n-th layer 2-5 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network 1, wherein values of the input layer 2 are given by the input of the neural network 1, wherein values of the first hidden layer 3 can be calculated based on the values of the input layer 2 of the neural network 1, wherein values of the second hidden layer 4 can be calculated based in the values of the first hidden layer 3, etc.

In order to set the values $w(m,n)_{i,j}$ for the edges 19-21, the neural network 1 has to be trained using training data. In particular, training data comprises training input data and training output data (denoted as $t_i$). For a training step, the neural network 1 is applied to the training input data to generate calculated output data. In particular, the training data and the calculated output data comprise a number of values, said number being equal to the number of nodes 17, 18 of the output layer 5.

In particular, a comparison between the calculated output data and the training data is used to recursively adapt the weights within the neural network 1 (backpropagation algorithm). In particular, the weights are changed according to $$w'_{i,j}{}^{(n)} = w_{i,j}{}^{(n)} - \gamma \cdot \delta_j{}^{(n)} \cdot x_i{}^{(n)}$$

wherein y is a learning rate, and the numbers $\delta(n)_j$ can be recursively calculated as $$\delta_j{}^{(n)} = (\Sigma_k \delta_k{}^{(n+1)} \cdot w_{j,k}{}^{(n+1)}) \cdot f'(\Sigma_i x_i{}^{(n)} \cdot w_{i,j}{}^{(n)})$$

based on $\delta(n+1)_j$, if the (n+1)-th layer is not the output layer 5, and $$\delta_j{}^{(n)} = (x_k{}^{(n+1)} - t_j{}^{(n+1)}) \cdot f'(\Sigma_i x_i{}^{(n)} \cdot w_{i,j}{}^{(n)})$$

if the (n+1)-th layer is the output layer 5, wherein f' is the first derivative of the activation function, and $y(n+1)_j$ is the comparison training value for the j-th node of the output layer 5.

Figure 5:
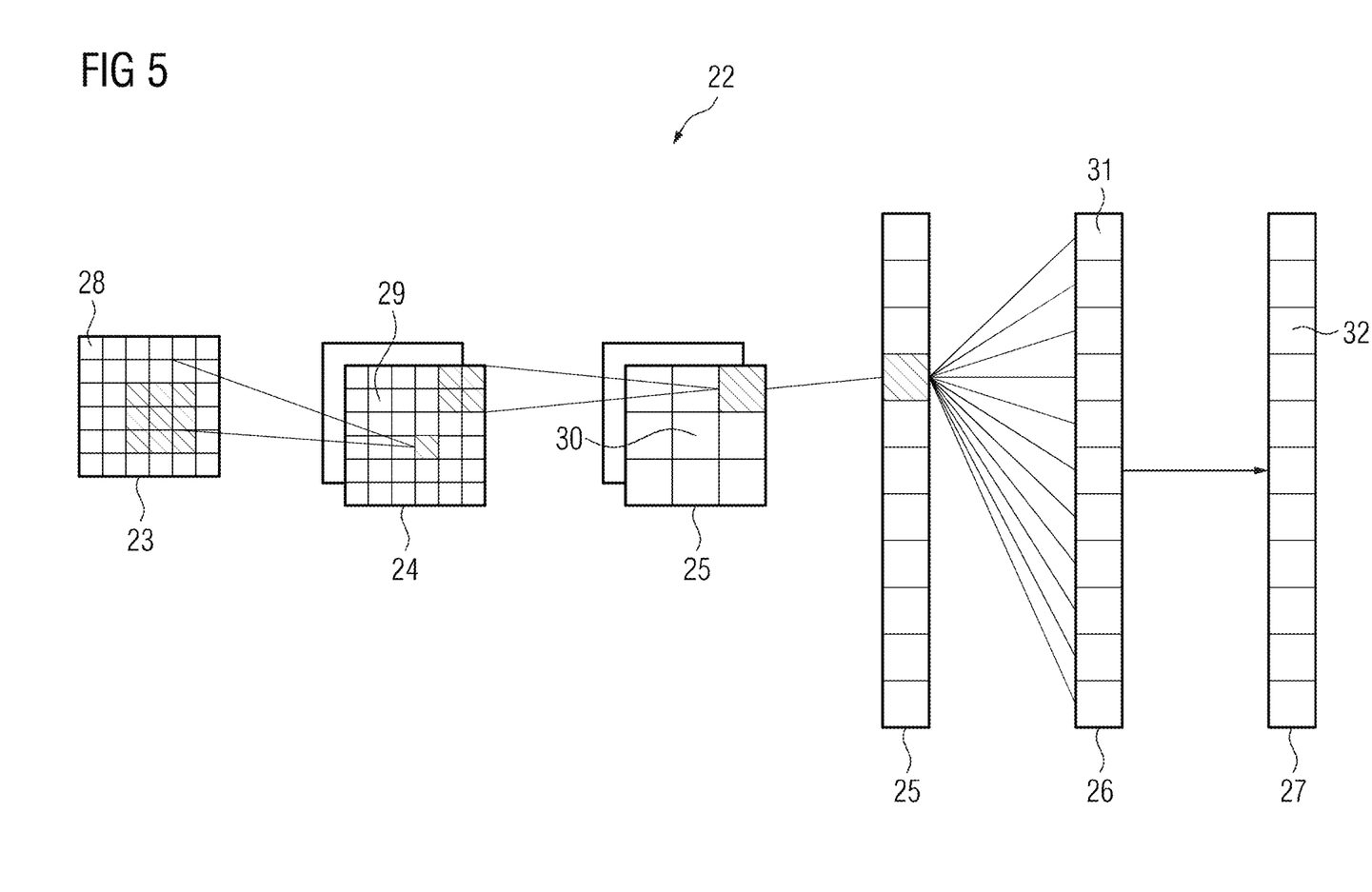

FIG. 5 displays an embodiment of a convolutional neural network 22. In the displayed embodiment, the convolutional neural network 22 comprises an input layer 23, a convolutional layer 24, a pooling layer 25, a fully connected layer 26 and an output layer 27. Alternatively, the convolutional neural network 22 can comprise several convolutional layers 24, several pooling layers 25 and several fully connected layers 26 as well as other types of layers. The order of the layers can be chosen arbitrarily, usually fully connected layers 26 are used as the last layers before the output layer 27.

In particular, within a convolutional neural network 22 the nodes 28-32 of one layer 23-27 can be considered to be arranged as a d-dimensional matrix or as a d-dimensional image. In particular, in the two-dimensional case the value of the node 28-32 indexed with i and j in the n-th layer 23-27 can be denoted as $x(n)[i,j]$. However, the arrangement of the nodes 28-32 of one layer 23-27 does not have an effect on the calculations executed within the convolutional neural network 22 as such, since these are given solely by the structure and the weights of the edges.

In particular, a convolutional layer 24 is characterized by the structure and the weights of the incoming edges forming a convolution operation based on a certain number of kernels. In particular, the structure and the weights of the incoming edges are chosen such that the values $x(n)_k$ of the nodes 29 of the convolutional layer 24 are calculated as a convolution $x(n)_k = K_k * x(n-1)$ based on the values $x(n-1)$ of the nodes 28 of the preceding layer 23, where the convolution * is defined in the two-dimensional case as $$x_k{}^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 28-32 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 28-32 in the respective layer 23-27. In particular, for a convolutional layer 24 the number of nodes 29 in the convolutional layer is equivalent to the number of nodes 28 in the preceding layer 23 multiplied with the number of kernels.

If the nodes 28 of the preceding layer 23 are arranged as a d-dimensional matrix, using a plurality of kernels can be interpreted as adding a further dimension (denoted as "depth" dimension), so that the nodes 29 of the convolutional layer 24 are arranged as a (d+1)-dimensional matrix. If the nodes 28 of the preceding layer 23 are already arranged as a (d+1)-dimensional matrix comprising a depth dimension, using a plurality of kernels can be interpreted as expanding along the depth dimension, so that the nodes 29 of the convolutional layer 64 are arranged also as a (d+1)-dimensional matrix, wherein the size of the (d+1)-dimensional matrix with respect to the depth dimension is by a factor of the number of kernels larger than in the preceding layer 23.

The advantage of using convolutional layers 24 is that spatially local correlation of the input data can exploited by enforcing a local connectivity pattern between nodes of adjacent layers, in particular by each node being connected to only a small region of the nodes of the preceding layer.

In the displayed embodiment, the input layer 23 comprises 36 nodes 28, arranged as a two-dimensional 6×6 matrix. The convolutional layer 24 comprises 72 nodes 29, arranged as two two-dimensional 6×6 matrices, each of the two matrices being the result of a convolution of the values of the input layer 23 with a kernel. Equivalently, the nodes 29 of the convolutional layer 24 can be interpreted as arranged as a three-dimensional 6×6×2 matrix, wherein the last dimension is the depth dimension.

A pooling layer 25 can be characterized by the structure and the weights of the incoming edges and the activation function of its nodes 30 forming a pooling operation based on a non-linear pooling function f. For example, in the two-dimensional case the values x(n) of the nodes 30 of the pooling layer 25 can be calculated based on the values x(n−1) of the nodes 29 of the preceding layer 24 as $$x^{(n)}[i,j]=f(x^{(n-1)}[id_1,jd_2], \ldots ,x^{(n-1)}[id_1+d_1-1,jd_2+d_2-1])$$

In other words, by using a pooling layer 25 the number of nodes 29, 30 can be reduced, by replacing a number d1·d2 of neighboring nodes 29 in the preceding layer 24 with a single node 30 being calculated as a function of the values of said number of neighboring nodes in the pooling layer 25. In particular, the pooling function f can be the max-function, the average or the L2-Norm. In particular, for a pooling layer 25 the weights of the incoming edges are fixed and are not modified by training.

The advantage of using a pooling layer 25 is that the number of nodes 29, 30 and the number of parameters is reduced. This leads to the amount of computation in the network 22 being reduced and to a control of overfitting.

In the displayed embodiment, the pooling layer 25 is a max-pooling, replacing four neighboring nodes with only one node, the value being the maximum of the values of the four neighboring nodes. The max-pooling is applied to each d-dimensional matrix of the previous layer 24; in this embodiment, the max-pooling is applied to each of the two two-dimensional matrices, reducing the number of nodes from 72 to 18.

A fully-connected layer 26 can be characterized by the fact that a majority, in particular, all edges between nodes 30 of the previous layer 25 and the nodes 31 of the fully-connected layer 26 are present, and wherein the weight of each of the edges can be adjusted individually.

In this embodiment, the nodes 30 of the preceding layer 25 of the fully-connected layer 26 are displayed both as two-dimensional matrices, and additionally as non-related nodes (indicated as a line of nodes, wherein the number of nodes was reduced for a better presentability). In this embodiment, the number of nodes 31 in the fully connected layer 26 is equal to the number of nodes 30 in the preceding layer 25. Alternatively, the number of nodes 30, 31 can differ.

Furthermore, in this embodiment the values of the nodes 32 of the output layer 27 are determined by applying the Softmax function onto the values of the nodes 31 of the preceding layer 26. By applying the Softmax function, the sum of the values of all nodes 32 of the output layer 27 is 1, and all values of all nodes 32 of the output layer 27 are real numbers between 0 and 1. In particular, if using the convolutional neural network 22 for categorizing input data, the values of the output layer can be interpreted as the probability of the input data falling into one of the different categories.

A convolutional neural network 22 can also comprise a ReLU (acronym for "rectified linear units") layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are $f(x)=\max(0,x)$, the tangent hyperbolics function or the sigmoid function.

In particular, convolutional neural networks 22 can be trained based on the backpropagation algorithm. For preventing overfitting, methods of regularization can be used, e.g. dropout of nodes 28-32, stochastic pooling, use of artificial data, weight decay based on the L1 or the L2 norm, or max norm constraints.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium, storage means or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the nontransitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Nonlimiting examples of the non-transitory computer-readable medium include, but are not limited to, rewriteable nonvolatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been described in detail with reference to example embodiments, the present invention is not limited by the disclosed examples from which the skilled person is able to derive other variations without departing from the scope of the invention.

The invention claimed is:

1. A computer implemented method for mapping a three-dimensional branched tubular structure in a three-dimensional image data set into at least one two-dimensional image plane, the method comprising:
  selecting a first group of voxels in the image data set based on segmentation data, the segmentation data describing a segmentation of the tubular structure in the image data set;

determining a respective transformation vector for each voxel of the first group using a given model, the given model specifying a respective position of at least part of the tubular structure in a respective image plane of the at least one two-dimensional image plane, wherein the respective transformation vector maps the respective voxel to the respective image plane;

selecting a second group of voxels in the image data set based on at least one of the image data set or the segmentation data, and determining a respective transformation vector for each voxel of the second group that maps the respective voxel to the image plane or a respective image plane, wherein at least one of the selection of the second group of voxels or the determination of the transformation vectors for the second group of voxels is performed by optimizing a cost function based on the transformation vectors for the first group of voxels; and generating at least one output image for the at least one image plane based on the first group of voxels, the second group of voxels, the transformation vectors for the first group of voxels and the transformation vectors for the second group of voxels.

2. The computer implemented method of claim 1, wherein the given model describes positions of centerlines of multiple segments of the tubular structure in the at least one image plane, and the selecting the first group of voxels selects voxels corresponding to at least a subgroup of the centerlines the first group of voxels based on the segmentation data.

3. A non-transitory computer-readable storage medium comprising instructions which, when executed by a data processing unit, cause the data processing unit to perform the method of claim 2.

4. The computer implemented method according to claim 1, wherein at least one of
 a sum of a number of voxels for the first group of voxels and the second group of voxels is equal to a number of pixels in the at least one output image, or
 the voxels the first group of voxels and the second group of voxels are mapped onto a regular, rectangular grid for each image plane.

5. The computer implemented method of claim 4, wherein the cost function includes a measure for a smoothness of a transformation from the three-dimensional image data set to the at least one two-dimensional image plane, the transformation being defined by the transformation vectors for the voxels of the first group and the transformation vectors for the voxels of the second group.

6. The computer implemented method according to claim 5, further comprising:
 determining a vector field for the transformation from the transformation vectors for the voxels of the first group and the transformation vectors for the voxels of the second group, wherein the measure for the smoothness is based on at least one of a first derivative of the vector field or a second derivative of the vector field.

7. The computer implemented method of claim 5, wherein for at least a subgroup of the second group of voxels the cost function is based on a distance of a respective voxel of the subgroup in the respective image plane of the at least one two-dimensional image plane from a position of at least voxel of the first group in the respective image plane or from at least one respective centerline described by the given model.

8. The computer implemented method of claim 7, wherein the cost function is based on a measure for a symmetry of the at least one output image.

9. The computer implemented method of claim 1, wherein the cost function includes a measure for a smoothness of a transformation from the three-dimensional image data set to the at least one two-dimensional image plane, the transformation being defined by the transformation vectors for the voxels of the first group and the transformation vectors for the voxels of the second group.

10. The computer implemented method according to claim 9, further comprising:
 determining a vector field for the transformation from the transformation vectors for the voxels of the first group and the transformation vectors for the voxels of the second group, wherein the measure for the smoothness is based on at least one of a first derivative of the vector field or a second derivative of the vector field.

11. The computer implemented method of claim 1, wherein for at least a subgroup of the second group of voxels the cost function is based on a distance of a respective voxel of the subgroup in the respective image plane of the at least one two-dimensional image plane from a position of at least voxel of the first group in the respective image plane or from at least one respective centerline described by the given model.

12. The computer implemented method of claim 1, wherein the cost function is based on a measure for a symmetry of the at least one output image.

13. The computer implemented method according to claim 1, wherein the cost function is based on a brightness of the at least one output image.

14. The computer implemented method of claim 1, wherein the selecting the second group of voxels selects the second group of voxels based on at least one of
 a brightness of the respective voxel,
 a proximity of the respective voxel to a voxel of the first group,
 a previously selected voxel of the second group,
 a segment of the image data set that is identified as part of the tubular structure, or
 a centerline of a segment of the tubular structure.

15. The computer implemented method of claim 1, further comprising:
 selecting one of a number of provided models based on at least one of the image data set or the segmentation data, the selected model at least one of (i) is used to determine the respective transformation vector for each voxel of the first group, or (ii) is parametrized based on at least one of the image data set or the segmentation data.

16. The computer implemented method of claim 1, wherein the image data set is a computed tomography dataset.

17. The computer implemented method according of claim 1, wherein the at least one output image is used as at least one of desired output data to train an algorithm by machine learning or input data of an algorithm trained by machine learning to determine at least one parameter of the three-dimensional branched tubular structure.

18. A device for mapping a three-dimensional branched tubular structure depicted in a three-dimensional image data set into at least one two-dimensional image plane, wherein the device configured to perform the computer implemented method of claim 1.

19. A non-transitory computer-readable storage medium comprising instructions which, when executed by a data processing unit, cause the data processing unit to perform the method of claim 1.

20. The computer implemented method according to claim 1, wherein the cost function is based on a brightness of the at least one output image.

* * * * *